United States Patent [19]

Mau et al.

[11] 4,001,332
[45] Jan. 4, 1977

[54] PROCESS FOR COMPRESSING KETENE

[75] Inventors: Günter Mau; Günter Jacobsen; Erich Brandes, all of Frankfurt am Main, Germany

[73] Assignee: Hoechst Aktiengesellschaft, Frankfurt am Main, Germany

[22] Filed: Dec. 9, 1975

[21] Appl. No.: 639,110

Related U.S. Application Data

[63] Continuation of Ser. No. 432,430, Jan. 10, 1974, abandoned.

[30] Foreign Application Priority Data

Jan. 13, 1973   Germany .......................... 2301655

[52] U.S. Cl. ............................................ 260/585.5
[51] Int. Cl.$^2$ ................... C07C 45/24; C07C 49/22
[58] Field of Search .................................. 260/585.5

[56] References Cited

UNITED STATES PATENTS 2,802,872   8/1957   Sturzenegger ................. 260/585.5

*Primary Examiner*—Norman Morgenstern
*Attorney, Agent, or Firm*—Curtis, Morris & Safford

[57] ABSTRACT

Ketene is compressed by means of a liquid ring pump using ketene-containing diketene as operating liquid.

6 Claims, 1 Drawing Figure

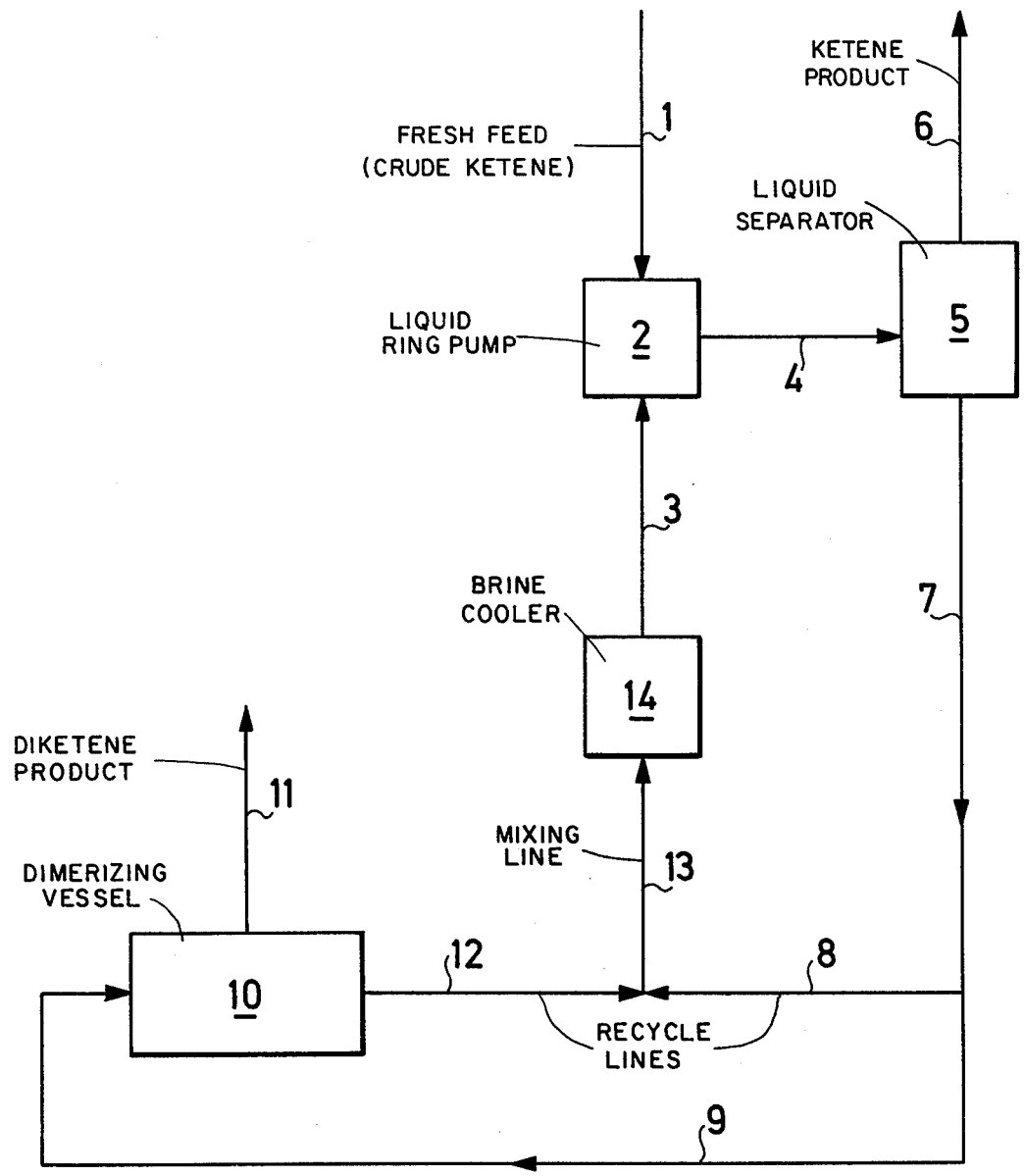

PROCESS FOR COMPRESSING KETENE

This is a continuation of application Ser. No. 432,430 filed Jan. 10, 1974 now abandoned.

The present invention is related to a process for compressing ketene by means of a liquid ring pump the operating liquid of which is constituted by ketene-containing diketenes.

A well known process for preparing ketene is based on the thermal cleavage of acetic acid under reduced pressure and in presence of catalysts, for example phosphoric acid alkyl esters. The thus produced water and the unreacted acetic acid as well as acetic anhydride obtained by a secondary reaction are condensed more or less completely, depending on the cooling efficiency of the condensers. A crude ketene of a concentration over 90% is obtained. As for the rest, it consists of a mixture of gases resulting from secondary reactions upon cleavage: carbon monoxide, ethylene, carbon dioxide, methane, allene and minor amounts of higher hydrocarbons, and of traces of acetic anhydride and diketene. Further processing requires the compression of the crude ketene obtained under a pressure of, for example, 100 (mm. Hg).

The compression of ketene constitutes a problem having no satisfactory solution so far because of the strong tendency of ketene to polymerize and/or resinify. Piston or rotary dry operation compressors are completely unsuitable for this purpose, since the narrow clearance is clogged by solid materials within moments. Attempts have been made to obviate this handicap by using lubricants or rinsing agents. Thus a process is already known which compresses ketene in a centrifugal piston pump or a rotary vane pump operated with paraffin oil or other lubricants. Such methods may well put off said difficulties; they are, however, unable to solve the problems. Consequently, involuntary operational interruption, due to a break-down of the vacuum pumps, are unavoidable.

A certain progress for compressing ketene has been made by using liquid piston type rotary gas blowers. Solid material cannot settle, due to the high turbulence of the abundantly present operating liquid which is, moreover, constantly changed and which rinses continuously the interior of the pump. But even this operation method has its problems.

The art knows, for example, a process for purifying ketene which comprises washing of the cracked gas with hexachlorobutadiene or ethers of aliphatic alcohols boiling over 130° C, after having eliminated the main quantities of water and acetic acid, while simultaneously compression is carried out in vacuum pumps, preferably in liquid piston type rotary blowers which are considered to be particularly appropriate. Subsequently, the washing liquid is cooled down, whereby the liquid impurities—mainly consisting of diketene and acetic anhydride—separate as second phase. The latter is separated and the washing liquid is recycled. An important inconvenience of the described process is the loss of part of the relatively expensive washing liquid as a consequence of separating the impurities. So as to keep the loss in reasonable limits, much cooling energy is needed. Furthermore, brine cooling is applied so that the compressed or purified ketene is freed of entrained washing liquid.

A variation of this process uses a mixture of hexachlorobutadiene and appropriate aliphatic hydrocarbons as washing and operating liquid. In that case, a water cooling system is sufficient for separating the impurities. The washing agent present in the phase which contains the impurities may be recuperated for re-use by addition of water.

Inconvenient are the increased requirements for apparatus equipment and the necessity to dose the water meticulously, on one hand, to avoid the separation of tar-like ketene-polymers and, on the other hand, to make sure that the hexachlorobutadiene-hydrocarbon-mixture present in the impurities is recuperated as completely as possible.

It is furthermore known that exclusive use is possible of hydrocarbons as washing and operating liquid. The hydrocarbons should not be too viscous and must not have an excessive steam pressure, because this operation method uses a liquid piston type rotary blower. The impurities of crude ketene are substantially insoluble in hydrocarbons. Therefore special processing steps for their separation are not necessary, and the losses in washing liquid are less high. But even this process does not overcome important deficiencies:

The phase separation is impeded by heavy foaming and as a result operating liquid is carried over in that very part of the apparatus where ketene must be cooled to low temperatures to free it from liquid constituents. When using fuel oils, crystals may form which are detrimental to the cooling effect or clog the cooling device.

The crucial point for the above mentioned processes is to bring the crude ketene from under reduced pressure to slight overpressure, if possible without any loss, so that it can be reacted with other materials. A process for reacting gases in liquids by means of a liquid piston type rotary blower is also known. Ketene can be reacted quantitatively with acetic acid in such a piston type rotary blower to yield acetic anhydride, in case that the operating liquid used for this reaction be acetic anhydride, that is the reaction product itself. This synthesis with ketene is only applicable to reactions in which the reaction product is appropriate for being used as operating liquid of a liquid piston type rotary blower.

Finally, while looking for a possibility to avoid materials alien to the reaction which must be used according to the above mentioned processes, a method has been proposed wherein the larger part of ketene is compressed and the smaller part reacted with an organic compound in liquid state. This latter acts here as washing liquid. However, the successful liquid piston type rotary blowers cannot be used for carrying through this process, since they need relatively important quantities of liquids for operation. Therefore, in these cases screw compressors, which are susceptible to trouble, have to be used.

Now, a process has been found for compressing ketene by means of a liquid ring pump wherein ketene-containing diketene is used as operating liquid.

The process according to the invention does not allow for recuperating at the exit of the pump the whole of ketene used in compressed state. Instead, part of the ketene is dissolved by the diketene used as operating liquid. This dissolved ketene dimerizes slowly to diketene in series-connected vessels, i.e. diketene is obtained besides ketene. This fact does not represent any disadvantage, since large-scale plants for the preparation of ketene are also producing diketene by dimerizing part of the ketene.

It is to be considered as especially advantageous that in the process according to the invention the proportion of the weight quantities of ketene and of diketene produced can be adapted according to the requirements.

A determined proportion of ketene to diketene is obtained by an appropriate mixture of diketene of two different kinds, one free of ketene, the other ketene-containing, and using this mixture as operating liquid for the liquid ring pump. A device suitable for carrying out the process of the invention is illustrated in the accompanying drawing.

Crude ketene under reduced pressure is aspirated by liquid piston type rotary blower 2 through pipe 1. The operating liquid for the ring pump is supplied through pipe 3. The mixture of gas and liquid is transported through pipe 4 to the liquid separator 5. The ketene adjusted to the desired overpressure escapes through pipe 6. The ketene-containing diketene flows off through pipe 7. It can be re-used via pipes 8 and 13 as operating liquid for the ring pump or transported through pipe 9 to the vessel 10 where the solution remains undisturbed and the ketene is transformed into diketene. The newly formed diketene flows off through pipe 11.

For a normal operation, both diketene charged with ketene as well as diketene practically free of ketene are mixed in pipe 13 for adjusting the operating liquid to the required ketene-concentration, the first being supplied through pipe 8 and the latter through pipe 12. The obtained mixture is fed into the ring pump after having traveled through the brine cooler 14 and pipe 3.

In case that the main interest is focused on preparing as much diketene as possible, the liquid ring pump 2 is supplied with diketene mainly through pipe 12. The larger part of ketene is then dissolved in the operating liquid and reaches vessel 10 through liquid separator 5 and pipes 7 and 9. If, on the contrary, the main interest goes to the preparation of ketene, the operating liquid is fed into the pump exclusively through pipe 8. The operating liquid already contains ketene in dissolved state, so that only a minor quantity of ketene to be compressed is dissolved, whilst the larger part of compressed ketene is ready for further syntheses.

In-between these two described extreme cases any desirable proportion of ketene and diketene may be adjusted by mixing the two streams of diketene from pipes 8 and 12 accordingly.

In comparison to the known methods, the process according to the invention offers quite a number of advantages. The compression of the ketene is carried out in a liquid ring pump with an operating liquid which does not introduce materials alien to the reaction and difficult to eliminate, so that a purification of the ketene—costly as well as prone to disturbances—such as cooling to low temperatures, is not necessary.

The impurities contained in the crude ketone such as acetic anhydride, diketene and polymeric constituents are absorbed by diketene in the liquid ring pump. The diketene is continuously formed and discharged, thus avoiding concentration of these materials in the cycle. The formerly known processes require the elimination of the impurities by separating two phases, a step difficulty manageable and a source of high losses, and for most of the syntheses the contaminated diketene has to be submitted to a purification by distillation.

The unexpected effect of the process according to the invention is illustrated by the following disclosure:

When introducing gas-containing liquids into the low pressure area of a liquid ring pump it should be expected that gas would escape from the liquid. This would increase the quantity of gas to be compressed and diminish the obtainable low pressure. It comes as a surprise that this effect occurs to a negligible extent only upon using ketene-containing diketene as operating liquid.

The crude ketene to be compresed is usually at a temperature between $-30°$ and $+50°$ C, preferably between $-10°$ and $0°$ C, and has a pressure of from 20 to 500 Torr, preferably from 70 to 130 Torr. The diketene used as operating liquid for the liquid ring pump is generally cooled prior to use to from $-8°$ to $+20°$ C, preferably from $-5°$ to $+5°$ C. The gas/liquid/mixture escaping from the pump on the pressure side is usually at about $0°$ to $50°$ C, preferably $10°$ to $20°$ C. The ketene is compressed under a pressure of preferably up to 1.2 atmospheres, but higher pressure levels are possible as well.

The following examples illustrate the invention; the percentages given are by weight.

EXAMPLES 1–4

100 kg of crude ketene per hour having a temperature of $-5°$ C are aspirated by a liquid ring pump. The crude ketene is of 93% strength and contains n% of a gas mixture consisting of carbon monoxide, ethylene, carbon dioxide, methane, allene and traces of higher hydrocarbons, as well as acetic anhydride and diketene.

The liquid ring pump is supplied with 2600 kg per hour of crude diketene (about 89% strength) having a temperature of $0°$ C so as to build up the liquid ring. The crude diketene represents a mixture of ketene-containing diketene from the liquid separator 5 and diketene free of ketene from the vessel 10. The gas/liquid/mixture leaves the ring pump at a temperature of about $15°$ C. The pressure of the ketene is adjusted to 1.03 atmospheres.

The examples summarized in the table show the dependency of produced proportion of ketene to diketene on the mixing proportion of diketene free of ketene to diketene containing ketene in the operating liquid for the liquid piston type rotary blower.

TABLE

| | parts operating liquid (kg) diketene (pipe 13) | | quantities prepared | | | | parts ketene + diketene (kg) calculated on pure materials (100 %) | preparation proportion | |
|---|---|---|---|---|---|---|---|---|---|
| | free of ketene | ketene-containing | ketene (pipe 6) | | diketene (pipe 11) | | | | |
| No. | (pipe 12) | (pipe 8) | parts (kg) | contents % | parts (kg) | contents % | | ketene | diketene |
| 1 | 1950 | 650 | 40 | 86 | 60 | 89 | 87 | 39 | 61 |
| 2 | 1300 | 1300 | 53 | 89 | 47 | 89 | 89 | 53 | 47 |
| 3 | 650 | 1950 | 65 | 91 | 35 | 89 | 90 | 66 | 34 |
| 4 | — | 2600 | 70 | 92 | 30 | 89 | 91 | 70 | 30 |

What is claimed is:

1. A process for compressing ketene which comprises: (a) introducing, as an operating liquid in a liquid ring pump, diketene; (b) compressing ketene, initially at a temperature between about −30° and 50° C. at a pressure between about 20 and about 500 mm. Hg in said liquid ring pump and obtaining said ketene as a compressed ketene at a temperature between −8° and 20° C. as a gas/operating liquid mixture having a temperature between 0° and 50° C, said diketene operating liquid being saturated with ketene under operating conditions at a pressure of up to about 1.2 atmospheres; (c) separating ketene from said operating liquid; and (d) recirculating said operating liquid to said liquid ring pump.

2. A process according to claim 1, wherein said gas-/operating liquid mixture is at a temperature between 10° and about 20° C.

3. A process according to claim 1, wherein said ketene is at a temperature between about −10° and about 0° C.

4. A process according to claim 1, wherein said ketene is initially at a pressure between about 70 and about 130 mm. Hg.

5. A process according to claim 1, wherein said operating liquid, diketene, is at a temperature between about −5° and about 5° C.

6. A process according to claim 1, wherein said gas-/operating liquid mixture is at a temperature between about 10° and about 20° C.

* * * * *